(12) United States Patent
Muhrer et al.

(10) Patent No.: US 8,182,792 B2
(45) Date of Patent: May 22, 2012

(54) PHARMACEUTICAL COMPOSITIONS

(75) Inventors: Gerhard Muhrer, Zürich (CH);
Ricardo Schneeberger, Wentzwiller (FR); Wolfgang Wirth, Arisdorf (CH); Anton Baumberger, Binningen (CH)

(73) Assignee: Novartis AG, Basel (CH)

( * ) Notice: Subject to any disclaimer, the term of this patent is extended or adjusted under 35 U.S.C. 154(b) by 1053 days.

(21) Appl. No.: 10/593,401

(22) PCT Filed: Mar. 22, 2005

(86) PCT No.: PCT/EP2005/003062
§ 371 (c)(1),
(2), (4) Date: Nov. 13, 2006

(87) PCT Pub. No.: WO2005/089718
PCT Pub. Date: Sep. 29, 2005

(65) Prior Publication Data
US 2008/0026981 A1    Jan. 31, 2008

(30) Foreign Application Priority Data

Mar. 23, 2004 (GB) .................................. 0406515.7
Nov. 9, 2004 (GB) .................................. 0424727.6

(51) Int. Cl.
*A61K 9/14* (2006.01)
(52) U.S. Cl. ........................... 424/46; 424/489; 424/490
(58) Field of Classification Search .................... 424/46, 424/489, 490
See application file for complete search history.

(56) References Cited

U.S. PATENT DOCUMENTS

| | | | |
|---|---|---|---|
| 6,135,628 A * | 10/2000 | DeStefano et al. | 366/176.1 |
| 6,177,103 B1 | 1/2001 | Pace et al. | |
| 6,228,346 B1 | 5/2001 | Zhang et al. | |
| 2007/0071826 A1 | 3/2007 | Kim | |
| 2008/0118442 A1 * | 5/2008 | Mohsen et al. | 424/46 |

FOREIGN PATENT DOCUMENTS

| | | |
|---|---|---|
| EP | 427680 | 5/1991 |
| EP | 0 768 114 | 4/1997 |
| EP | 0 726 088 | 6/2003 |
| JP | 61136534 | 6/1986 |
| JP | 08-511987 | 12/1996 |
| JP | 09-122466 | 5/1997 |
| JP | 2002-511398 | 4/2002 |
| JP | 2002-518318 | 6/2002 |
| JP | 2006-517465 | 7/2006 |
| JP | 2007-503399 | 2/2007 |
| JP | 2007-518706 | 7/2007 |
| WO | WO-95/01221 | 1/1995 |
| WO | WO 99/11605 | 3/1999 |
| WO | WO-99/52504 | 10/1999 |
| WO | WO 99/65469 | 12/1999 |
| WO | WO-99/65469 | 12/1999 |
| WO | 00/25746 | 5/2000 |
| WO | 00/61275 | 10/2000 |
| WO | WO 00/75114 | 12/2000 |
| WO | WO 02/00679 | 1/2002 |
| WO | WO 2004/005281 | 1/2004 |
| WO | WO 2004/016601 | 2/2004 |
| WO | WO-2004/062785 | 7/2004 |
| WO | 2004/108266 | 12/2004 |
| WO | WO-2005/018611 | 3/2005 |

OTHER PUBLICATIONS

Humerov, F.M., "Sub-and supercritical fluids in processes of treating polymers," Introduction. Publ. by FEN 2000, Journal of Chemistry and Computer Simulation. Butlerov Communications, No. 1, vol. 5. 2004. (English Abstract only).
International Search Report and Written Opinion received for Intl. Appln. No. PCT/EP2005/003062, mailed Jun. 26, 2006, 11 pp.
Search Report received for United Kingdom Appln. No. GB0406515.7 dated Jul. 19, 2004, 1 p.
Search Report received for United Kingdom Appln. No. GB0424727.6 dated Mar. 4, 2005, 1 p.

* cited by examiner

*Primary Examiner* — Mina Haghighatian
(74) *Attorney, Agent, or Firm* — Foley & Lardner LLP

(57) ABSTRACT

A process for micronization of pharmaceutically active agents.

19 Claims, 3 Drawing Sheets

PHARMACEUTICAL COMPOSITIONS

The present invention relates to a process for preparing small particles of pharmaceutically active agent, e.g. having an average particle size of from less than about 7 micrometers, to particles of pharmaceutically active agents prepared by said process and to pharmaceutical compositions comprising said particles.

The controlled production of particles of pharmaceutically active agents having a defined particle size in the low micron or submicron size range presents specific technical difficulties. Conventional crushing, grinding as well as wet and dry milling processes are often associated with more or less severe operational problems or poor product quality due to e.g. heavy metal contamination when organic pharmaceutical compounds and active agents are handled.

For example, milling techniques are frequently used in industrial practice to reduce particle size of solids. However, dry milling techniques may cause unacceptable levels of dust which require sophisticated safety precautions to be taken during milling operation. Moreover in many cases, dry milling increases the amorphous content in particulate formulations of pharmaceutically active agents, which may not be advantageous or entail weakened or even adverse therapeutic effects. Dry milling processes often suffer from significant product loss or from operational problems such as product caking or equipment clogging. The latter is frequently observed when adhesive, sticky powders are handled in conventional dry milling equipment. The main limitation of wet milling technology is heavy metal contamination due to direct physical contact of the particles with the grinding media as well as wall attrition. Other technical problems observed in dry and wet comminution of pharmaceutically active agents are thermal and chemical degradation due to e.g. local high temperatures in the milling equipment, non-uniform product characteristics, and batch-to-batch variability.

Spray and freeze drying techniques or particle formation using supercritical fluids have been used as alternative processes to produce micronized dry powders. However, all three technologies hardly ever match the requirements with respect to average particle size. Moreover, thermally labile molecules may be prone to decomposition or degradation upon exposure to elevated temperatures that are typically used in spray drying. Similarly, an often undesired increase of the amorphous content in the formulation is often observed in both spray and freeze drying as well as in particle formation with supercritical fluids.

There is a need to provide robust and simple processes for the industrial production of micron or submicron size particles of difficult-to-comminute pharmaceutically active agents with a controlled average particle size and controlled particle size distribution (PSD) which overcome these technical problems. The present invention provides a process which avoids or minimizes the above technical problems.

In one aspect the present invention provides a process for the controlled micronization of pharmaceutically active agent, e.g. having an average particle size of less than about 7 micrometers, e.g. from about 0.1 or 0.5 to about 1, 2, 3, 4, 5, 5.5, 6, or 6.5 micrometers, comprising (a) suspending the pharmaceutically active agent in a compressed gas or propellant, (b) processing the suspension by high pressure homogenization and (c) obtaining dry powder from the process upon depressurization.

In another aspect the present invention provides a process for the controlled micronization of pharmaceutically active agent, e.g. having an average particle size of less than 7 micrometers, e.g. from about 0.1 or 0.5 to about 1, 2, 3, 4, 5, 5.5, 6, or 6.5 micrometers, comprising (a) suspending the pharmaceutically active agent in a propellant, (b) processing the suspension by high pressure homogenization and (c) obtaining a suspension of the micronized pharmaceutically active agent in a propellant.

The pharmaceutically active agent may be suspended in a compressed gas or propellant and optionally one or more pharmaceutically acceptable excipient(s) may be used to form the suspension media.

The invention may be practiced with a wide variety of pharmaceutically active agents. The drug substance is preferably present in an essentially pure form. The particle size of the drug substance powder is reduced by the process of the invention to an average particle size of less than about 7 micrometers, e.g. of about 0.1 or 0.5 to about 1, 2, 3, 4, 5, 5.5, 6 or 6.5 micrometers, e.g. from about 0.5 to about 5.0 micrometers, from coarse starting material with average particle sizes between about 10 to 200 micrometers, preferably from between about 10 to 40 micrometers. The process of the present invention may preferably be used to micronize high-aspect-ratio, spicular or needle-like crystals. Particles exhibiting such or similar morphology often cause severe operational problems in conventional milling equipment. In particular, equipment clogging or malfunction due to the formation of a compressed bulky powder cake inside the mill are frequently observed. Furthermore, the process of the present invention is particularly suitable to micronize very adhesive or sticky drug substances which frequently entail similar or other operational problems.

For the purpose of the invention "pharmaceutically active agent" means all substances that produce a pharmaceutical or a therapeutic effect. Examples of pharmaceutically active agents include but are not limited to poorly water soluble and/or thermally or chemically unstable active agents, such as e.g. phenytoin (5,5-diphenylhydantoin), $\beta_2$-adrenoreceptor agonists such as compounds (in free or salt or solvate form) of formula I of WO 2000/075114, preferably compounds of the Examples thereof, especially a compound of formula

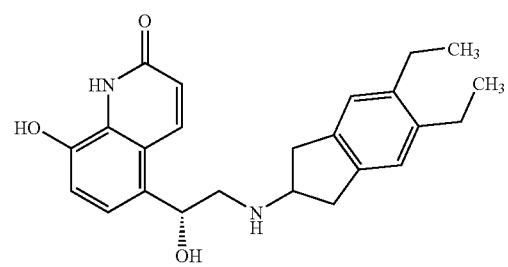

and pharmaceutically acceptable salts thereof, as well as compounds (in free or salt or solvate form) of formula I of WO 2004/016601, preferably compounds of the Examples thereof, especially those of Examples 1, 3, 4, 5 and 79; corticosteroids such as compounds (in free or salt or solvate form) of formula I of WO 2002/000679, preferably compounds of the Examples thereof, especially those of Examples 3, 11, 14, 17, 19, 26, 34, 37, 39, 51, 60, 67, 72, 73, 90, 99 and 101; anti-muscarinic antagonists such as compounds (in salt or zwitterionic form) of formula I of PCT/EP2004/004605, preferably compounds of the Examples thereof, especially those of Examples 17, 34, 52, 54, 71, 76, 96, 114, 138, 159, 170, 190, 209, 221, 242 and 244; pimecrolimus (33-Epichloro-33-desoxy-ascomycin) as described in e.g. EP 427680; N-benzoylstaurosporine as described in e.g. EP 296110; proteins; peptides; vitamins; steroids; corticosteroids and bronchodilators.

Further pharmaceutically active agents may include but are not limited to oxcarbazepine, carbamazepine, 1-(2,6-Difluoro-benzyl)-1H-[1,2,3]triazole-4-carboxylic acid amide; pyrimidylaminobenzamides such as compounds of formula I of WO 04/005281, preferably compounds of the Examples thereof, especially those of Example 92; Cox-2 selective inhibitors e.g. 5-methyl-2-(2'-chloro-6'-fluoroanilino) phenyl acetic acid as described in e.g. WO 99/11605; a camptothecin derivative having the following structure known as Compound A:

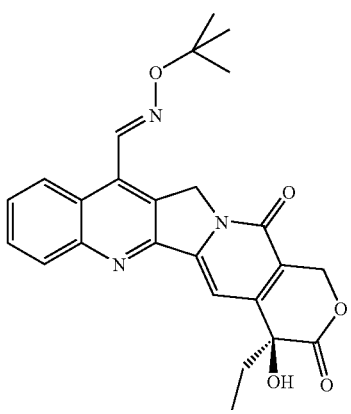

Compound A

Compound A may be in free or pharmaceutically acceptable salt form, and may be prepared as described in U.S. Pat. No. 6,424,457. Compound A may be in the form of their possible enantiomers, diastereoisomers and relative mixtures, the pharmaceutically acceptable salts thereof and their active metabolites.

The pharmaceutically acceptable excipient may be a surfactant. Suitable surfactants include acetylated monoglycerids such as for example the surfactant known and commercially available under the trade name Myvacet® 9-08, (Fiedler loc. cit., p 1167), perfluorocarboxilic acid, polyethylene glycol (PEG) sterol esters e.g. PEG 200, 300, 400 or 600 (Fiedler loc. cit., p 1348), polyethylene oxide sorbitan fatty acid esters e.g. Tween® 20, 40, 60, 65, 80 or 85 (Fiedler loc. cit. pp 1754), sorbitan esters e.g. sorbitan mono laureate, sorbitan mono oleate, sorbitan tri oleate or sorbitan mono palmitate, propylene glycol and oleic acid. Optionally a combination of one or more surfactants may be used.

In another aspect of the invention the excipient may be a carrier. Carriers may be composed of one or more crystalline sugars, e.g. of one or more sugar alcohols or polyols. Preferably lactose or glucose may be used.

In a further aspect of the invention the excipient may be an anti-friction or anti-adhesion agent such as a lubricant. Suitable lubricants include leucine, lecithin, magnesium stearate, stearic acid, sodium lauryl sulfate, sodium stearyl fumarate, stearyl alcohol, sucrose mono palinate, menthol, colloidal silicon dioxide, e.g. as commercially available under the trade name Aerosil® 200, and sodium benzoate or a combination thereof.

In a further aspect the excipients may include antimicrobial agents, e.g. benzalconium chloride, acidifiers, e.g. citric acid, antioxidants, e.g. ascorbic acid, chelating agents, e.g. disodium EDTA.

The excipients may include a combination of one or more additives.

Details of suitable excipients for use in the process of the invention are described in Fiedler's "Lexikon der Hilfsstoffe", $5^{th}$ Edition, ECV Aulendorf 2002 and the "Handbook of Pharmaceutical Excipients", Rowe, Sheskey and Weller, $4^{th}$ Edition 2003 which are hereby incorporated by reference.

In one embodiment of the invention the powder of the pharmaceutically active agent used in the process of the present invention is suspended in a compressed gas. The amount of active agent suspended in a compressed gas may range from about 0.1% grams per liter (0.01% per volume) to about 250 grams per liter (25% per volume).

One class of compressed gases includes $CO_2$, ethane, propane, butane, dimethyl ether and nitrogen. A combination of compressed gases may also be used. Preferably $CO_2$ may be used.

Another class of compressed gases are propellants, including hydrofluoroalkanes (HFA) e.g. 1,1,1,2-tetrafluoroethane (HFA 134a) and 1,1,1,2,3,3,3-heptafluoropropane (HFA 227). HFA 134a and HFA 227 are qualified for human use, and in contrast to chlorofluorocarbon (CFC) propellants they have no depleting effect on the ozone layer. Further examples of hydrofluoroalkane propellants are perfluoroethane, monochlorodifluoromethane and difluoroethane. A combination of propellants may also be used.

For the purpose of the invention "suspension" means a two phase system consisting of a finely divided solid dispersed in a continuous, e.g. compressed, gas phase.

The suspension may be prepared by loading the coarse starting material into a stirred pressure vessel. The vessel may be closed and tightly sealed to allow operation at elevated pressure, and the compressed gas may be added to form the suspension. The operating pressure in the stirred vessel may depend on the compressed gas. Typical operating pressures at room temperature according to the invention may range from 1.5 to 2 bars to about 300 bars, e.g. from about 10 to about 30 bars for some hydrofluoroalkanes, e.g. from about 55 to about 60 bars for carbon dioxide, and e.g. from about 200 bars to about 300 bars for nitrogen. Operating pressures may range from about 2 to about 5 bars in the case of hydrofluoroalkanes if the operating temperature is significantly below room temperature, e.g. from about 0 to 5° C. Suitable operating temperatures for the proposed process may range from about −30° C. to about 50° C. The entire process may be carried out in tightly closed and sealed, pressure-proof equipment.

High pressure homogenization is an established technology for preparing o/w, w/o, s/o/w, or w/o/w emulsions, solid-lipid nanoparticles, stabilized suspensions, and deagglomeration of solids dispersed in aqueous suspensions. In conventional high pressure homogenization suspensions of solids or of liquids in liquids are first formed and then processed in the homogenization unit at elevated pressures of up to several thousand bars.

According to the present invention, high pressure homogenization of compressed gas suspensions may be an effective technology to produce micronized particles of a pharmaceutically active agent, e.g. with a defined product particle size of less than about 7 micrometers, e.g. of from about 1 or 2 to about 3, 4, 5, 5.5, 6, or 6.5 micrometers from coarse starting material with an average particle sizes from about 10 to about 200 micrometers. The average particle size and the particle size distribution of the product, which may be harvested as a dry powder after depressurization of the unit or as a compressed gas suspension, may be efficiently controlled by closely controlling the characteristic process parameters of the proposed micronization process. Homogenization pressure, suspension density and solids concentration, operating temperature, choice of interaction geometries and number of passes through the equipment (which is largely equivalent to total processing time) or combinations of these main operating parameters may be used to closely control product quality. The process of the invention may be used to generate narrow particle size distributions in the size range of less than 7 micrometers, e.g. of about 1 or 2 to about 3, 4, 5, 5.5, 6 or 6.5 micrometers. The size range of about 1 to about 5 micrometers may be particularly suitable for application in therapeutic inhalation formulations, e.g. in dry powder inhalers (DPI) or in metered-dose inhalers (MDI) or pressurized metered-dose inhalers (pMDI).

In a further aspect the present invention provides an apparatus for micronization of pharmaceutically active agents comprising one or two stirred pressure vessels, a high pressure homogenizer, and a fluid conduit interconnecting the stirred pressure vessel or stirred pressure vessels and the high pressure homogenization unit. The stirred pressure vessel used to prepare the suspension of the starting material may be connected to a line supplying sufficient amounts of compressed gas, which itself may be connected to one or several dip-tube or gas cylinders, or a surge tank containing the pressurized gas. The desired operating pressure may be set and controlled by adding compressed gas through a pump until the set point may be reached. The high pressure homogenization unit may include an intensifier pump, and one or multiple interaction chambers, where the particle size reduction or micronization takes place due to particle-particle and particle-wall collisions, shear forces, and fluid cavitation. The intensifier pump, the line connecting the stirred pressure vessel and the intensifier pump of the high pressure homogenization unit may be cooled to avoid compressible gas bubbles accumulate in the inlet section of the intensifier pump. The high pressure homogenization unit may include a further intensifier pump. Homogenization may be achieved by adjusting a defined pressure drop of less than e.g. 1500 bars, e.g. of 200, 500, 750, 1000 or 1500 bar, across a high pressure gap or valve of static geometry. A dynamic high pressure homogenization valve may be used. This valve overcomes some of the major disadvantages of static interaction geometries, such as clogging at elevated solids concentrations. In case of blocking, the valve is opened, and the desired pressure drop may be readjusted manually or automatically using a suitable pressure control device.

The interaction chambers may provide a stream splitter and an impaction chamber. The stream of compressed gas, nonsolvent containing the solid particles and optionally pharmaceutically acceptable excipients may be splitted into two substreams in the stream splitter, and these two streams may be rejoined in the impaction chamber. The primary forces causing micronization of solid particles in the high pressure homogenizer may be shear forces, turbulent flow, acceleration and velocity change in flow direction; impact forces, involving collision of the processed particles processed with solid elements of the homogenizer, and collision between the particles being processed; and cavitation forces, involving an increased change in velocity with a decreased change in pressure, and turbulent flow. An additional force may be attributed to attrition, i.e. grinding by friction.

If micronization is achieved by releasing the pressure across a defined gap, such as for example a high pressure valve, the primary forces causing micronization may be cavitation, shear forces, turbulence, impact forces involving collision of the processed particles with solid elements of the homogenizer, and collision between the particles being processed, as well as attrition.

In one embodiment of the present invention the process may be carried out in an apparatus consisting of one stirred pressure vessel and a high pressure homogenization unit. The outlet of the homogenizer may be connected to the stirred pressure vessel containing the suspension. The processed suspension is re-introduced into the vessel containing unprocessed suspension. Total processing time may be used to control the average particle size of the particulate product or the particles in compressed gas suspension. The operation of the high pressure homogenizer may be initiated after a suspension of the active agent in the compressed gas has been formed in the pressure vessel. The homogenizer may operate as follows: The homogenizer which has an inlet and an outlet relies on a high pressure pump which is designed to supply the desired pressure at a constant rate to the product stream. The pump delivers the product at constant pressure through defined fixed geometry microchannels within the interaction chamber. Particle size reduction and homogenization of the suspension formed previously in the stirred pressure vessel occur within the interaction chamber. The jet interaction chamber block makes use of three different forces: shear, impaction and cavitation. The high pressure homogenization provides rather uniform particle size reduction e.g. micronization and deagglomeration of the pharmaceutically active agent.

In another embodiment of the invention, referring to FIG. 1, the apparatus may consist of two stirred pressure (10) vessels, that are provided with stirrer means (16), and a high pressure homogenization (12) unit. The inlet and the outlet of the homogenizer (12) may be connected by high pressure tubing (15) to both stirred pressure vessels (10), and all connections may be shut off individually by operating a high pressure three-way valve (11) or high pressure valves (17) manually or automatically. The suspension of the starting material may be formed in one of the two stirred pressure vessels, and then homogenization may be initiated. The outlet of the homogenizer may be connected to the second pressure vessel, which is initially empty. If the first stirred pressure vessel is empty and the second stirred pressure vessel is full with homogenized suspension, the valves may be operated such as to re-direct the contents of the second stirred pressure vessel containing the homogenized suspension through the homogenizer, and collect the twice homogenized suspension in the first stirred pressure vessel. The advantage of this embodiment of the invention is a more efficient control of the average particle size by controlling the residence time through the number of passes through the equipment. Average particle size in this embodiment is controlled by the total number of passes through the homogenizer, and typical numbers of passes in practice range from about 3 to 25 to reach an average particle size of less than about 7 micrometers, e.g. from about 0.1 or 0.5 to about 1, 2, 3, 4, 5, 5.5, 6 or 6.5 micrometers. If the total number of passes through the homogenizer is reached the suspension may be stored in a storage tank (14). In this embodiment of the invention both static interaction geometries and dynamic high pressure relaxation valves may be used for homogenization.

The high pressure homogenizer featuring static interaction geometries may be, for example, a closed system, e.g. a Microfluidics Model M-110Y Microfluidizer®. The apparatus and method of operation of a Microfluidizer® is further described in U.S. Pat. No. 4,533,254 and in U.S. Pat. No. 4,908,154 which are hereby incorporated by reference. Membrane pumps may also be used in conjunction with the Microfluidics M-110Y Microfluidizer® interaction geometries instead of the original high pressure piston pump.

A dynamic high pressure homogenizer may be, for example, a system comprising a high pressure intensifier pump, e.g. a LEWA LDE/1V M211S membrane dosage pump, and a suitable high pressure valve with adjustable valve opening or gap, and valve seat and body are preferably made of cavitation-resistant materials such as e.g. zirconium oxide, tungsten carbide or materials of similar quality. The material of the valve needle or plunger may preferably be made of harder material than the valve seat. The dynamic high pressure valve may be operated manually or automatically by using suitable means of downstream pressure control.

In another aspect of the invention the process of the present invention provides solvent- and moisture-free dry particles of the pharmaceutically active agent having an average particle size of less than about 7 micrometers, e.g. from about 1 or 2 micrometers to about 3, 4, 5, 5.5, 6 or 6.5 micrometers obtained by depressurization of the system. The pharmaceutically active agent powder particles of a size of about 1 to about 5 micrometers may be used for dry powder inhaler (DPI) formulations without any further processing.

In a further aspect of the invention the process provides particles of the pharmaceutically active agent having an average particle size of less than about 7 micrometers, e.g. from about 0.1 or 0.5 micrometers to about 1, 2, 3, 4, 5, 5.5, 6 or 6.5 micrometers finely dispersed in a propellant qualified for human use to form a suspension. The suspension comprising particles of a size of about 0.5 to about 5 micrometers may be filled directly into suitable inhalation devices, and then used in metered-dose (MDI) or pressurized metered-dose inhaler (pMDI) formulations without any further post-processing.

One advantage of the present invention is that the suspension of the pharmaceutically active agent in the propellant or compressed gas may be micronized in a single step process avoiding the need for any additional post-processing steps. Upon depressurization of the compressed gas or the propellant dry powder of the pharmaceutically active agent is obtained which may be used for inhalation formulation without any further processing. The process is easy to apply and perform under mild and inert conditions. Technical problems such as high amounts of solvents, increase of amorphous content, contamination and attrition are avoided by the process of the present invention.

In a further aspect the invention provides a pharmaceutical composition comprising micronized pharmaceutically active agent particles obtained by the process of the present invention and pharmaceutically acceptable excipients. The pharmaceutically acceptable excipients as described above include surfactants, carriers and/or lubricants, and may be used to produce a pharmaceutical composition, e.g. in the form of solid dosage forms such as capsules, tablets or sachets.

In a further aspect the invention provides micronized particles of a pharmaceutically active agent to be used in an ointment or an eye drop formulation.

In a another aspect the invention provides micronized particles of a pharmaceutically active agent to be used in parenteral formulations.

In a another aspect the invention provides micronized particles of a pharmaceutically active agent to be used in oral formulations.

In a another aspect the invention provides micronized particles of a pharmaceutically active agent to be used in topical formulations.

In a further aspect the invention provides a package comprising a composition of the invention together with instructions for use.

The structure and advantages of the present invention will become further apparent upon consideration of the following non-limiting description of several embodiments of the present invention in conjunction with the accompanying drawings.

Following is a non-limiting description by way of example.

EXAMPLE 1

Pimecrolimus is suspended in the propellant HFA227 (1,1,1,2,3,3,3-heptafluoropropane) and homogenized in a Microfluidics Microfluidizer M-110™. One pressure vessel is used, and the total processing time is 60 minutes. The operating pressure in the stirred vessel is about 3 bars, and the maximum homogenization pressure is about 500 bars. The inlet temperature is 0° C., and the outlet temperature is approximately 30° C. The pressure vessel is depressurized after 60 minutes of processing, and the dry product powder is analyzed using standard off-line analytical tools.

EXAMPLE 2

Pimecrolimus is suspended in the propellant HFA227 (1,1,1,2,3,3,3-heptafluoropropane) and homogenized in a Microfluidics Microfluidizer M-110™. Two pressure vessels are used, and the number of passes through the equipment is used to control the average particle size of the product. The operating pressure is about 3 bars, and the maximum homogenization pressure is about 500 bars. The inlet temperature is about 0° C., and the outlet temperature is about 30° C. After the $10^{th}$ pass, the system is depressurized, and the dry product powder is analyzed using standard off-line analytical tools.

EXAMPLE 3

Pimecrolimus is suspended in the propellant HFA134 (1,1,1-trifluoroethane) and homogenized across a high pressure valve at closely controlled pressure drop. One pressure vessel is used, and the total processing time is 180 minutes. The operating pressure is about 10 bars, and the maximum homogenization pressure is about 750 bars, thus using a pressure drop of about 740 bars across the relaxation valve. The inlet temperature is about 0° C., and the outlet temperature is about 30° C. The pressure vessel is depressurized after 180 minutes of processing, and the dry product powder is analyzed using standard off-line analytical tools.

Pimecrolimus particles as obtained in Example 1, 2 and 3 are re-dispersed in water containing about 0.1% Tween 20 to form a suspension, and then ultrasonicated for typically 60 seconds prior to measuring particle size using a Sympatec Helos laser-light diffraction particle sizer. The results of the particle size measurement are illustrated in Table 1. The processing time is 60 minutes in continuous mode in the run as described in Example 1, and the average particle size by volume ($x_{50}$) is 2.7 micrometers and $x_{90}$ is 11.4 micrometers. In the run as described in Example 2, the sample is processed in batch-mode, and results after 10 passes are reported. In this case, $x_{50}$ is 5.3 (5.5) micrometers and $x_{90}$ is 19.2 (20.6) micrometers.

TABLE 1

| Run No./Measurement No. | Processing Mode | $x_{10}$ [μm] | $x_{50}$ [μm] | $x_{90}$ [μm] |
|---|---|---|---|---|
| 1/1 | 60 min. | 0.9 | 2.7 | 11.4 |
| 1/2 | 60 min. | 0.9 | 2.7 | 11.7 |

TABLE 1-continued

| Run No./<br>Measurement No. | Processing<br>Mode | $x_{10}$ [μm] | $x_{50}$ [μm] | $x_{90}$ [μm] |
|---|---|---|---|---|
| 2/1 | 10 passes | 1.1 | 5.5 | 20.6 |
| 2/2 | 10 passes | 1.0 | 5.3 | 19.2 |
| 3/1 | 180 min | 0.89 | 2.13 | 6.07 |

EXAMPLE 4

Phenytoin (5,5-diphenylhydantoin) is suspended in propellant HFA134 (1,1,1-trifluoroethane) and homogenized across a high pressure valve at closely controlled pressure drop. One pressure vessel is used, and the total processing time is 240 minutes. The operating pressure is about 10 bars, and the maximum homogenization pressure is about 750 bars. The inlet temperature is about 0° C., and the outlet temperature is about 30° C. The pressure vessel is depressurized after 240 minutes of processing, and the dry product powder is analyzed using standard off-line analytical tools. The particle size distribution of phenytoin microparticles produced in example 4 is illustrated in FIG. 2.

EXAMPLE 5

Phenytoin (5,5-diphenylhydantoin) is suspended in carbon dioxide and homogenized across a high pressure valve at closely controlled pressure drop. One pressure vessel is used, and the total processing time is 240 minutes. The operating pressure is about 57 bars, and the maximum homogenization pressure is about 800 bars. The inlet temperature is about 0° C., and the outlet temperature is about 30° C. The pressure vessel is depressurized after 240 minutes of processing, and the dry product powder is analyzed using standard off-line analytical tools. The particle size distribution of phenytoin microparticles produced in example 5 is illustrated in FIG. 3.

Phenytoin particles as obtained in Example 4 and 5 are re-dispersed in water containing about 0.1% Tween 20 to form a suspension, and then ultrasonicated for typically 60 seconds prior to measuring particle size using a Sympatec Helos laser-light diffraction particle sizer. The results of the particle size measurement are illustrated in Table 2. The processing time is 240 minutes in continuous mode in the runs as described in Examples 4 and 5, and the average particle size by volume ($x_{50}$) is 1.48 and 1.46 micrometers, respectively, and $x_{90}$ is 3.57 and 3.02 micrometers, respectively.

TABLE 2

| Run No./<br>Measurement No. | Processing<br>Mode | $x_{10}$ [μm] | $x_{50}$ [μm] | $x_{90}$ [μm] |
|---|---|---|---|---|
| 4 | 240 min. | 0.72 | 1.48 | 3.57 |
| 5 | 240 min. | 0.73 | 1.46 | 3.02 |

Figure 1:
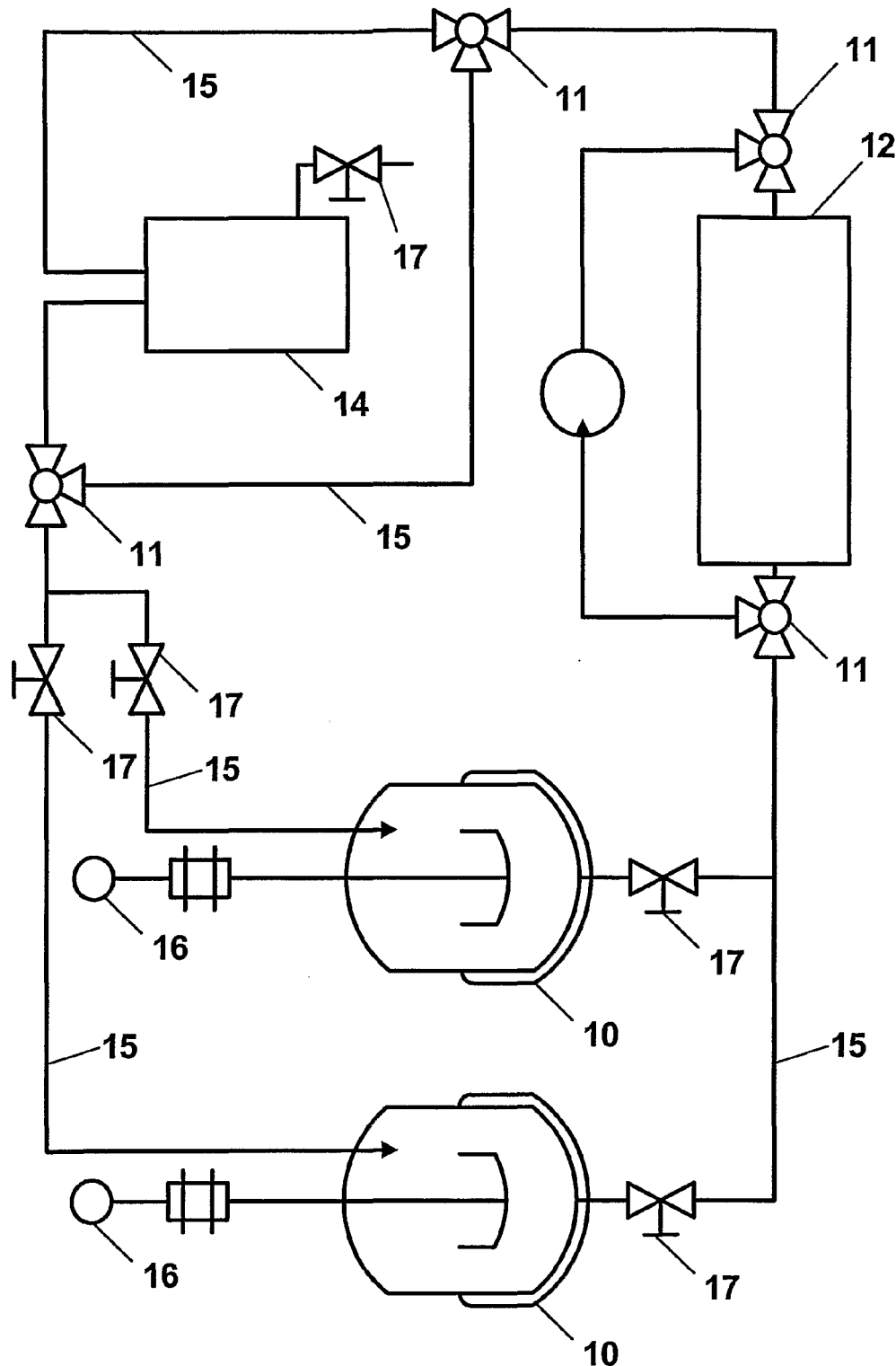
FIG. 1 is a schematic drawing of a closed, continuous-loop apparatus comprising two stirred pressure vessels in accordance with the invention. The apparatus consists of two stirred pressure (10) vessels, that are provided with stirrer means (16), a high pressure homogenization (12) unit and a storage tank (14). The inlet and the outlet of the homogenizer (12) are connected by high pressure tubing (15) to both stirred pressure vessels (10), and all connections are shut off individually by operating a high pressure three-way valve (11) or high pressure valves (17) manually or automatically.
Figure 2:
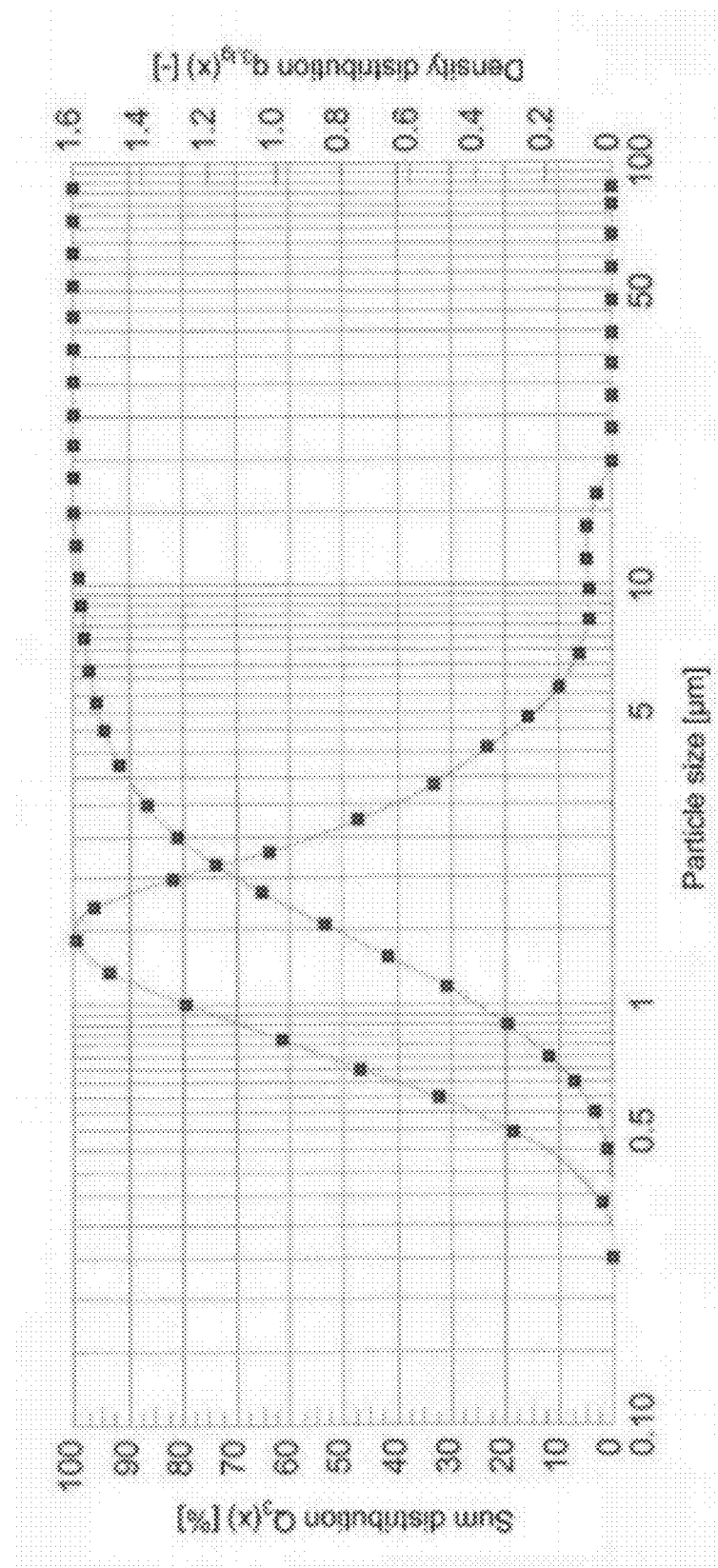
FIG. 2 is an example of phenytoin microparticles produced using a process of the invention. In example 4, the particle size distribution measured using a Sympatec Helos laser light diffraction particle sizer is as follows: $x_{10}$=0.72 micrometers, $x_{50}$=1.48 micrometers, and $x_{90}$=3.57 micrometers.
Figure 3:
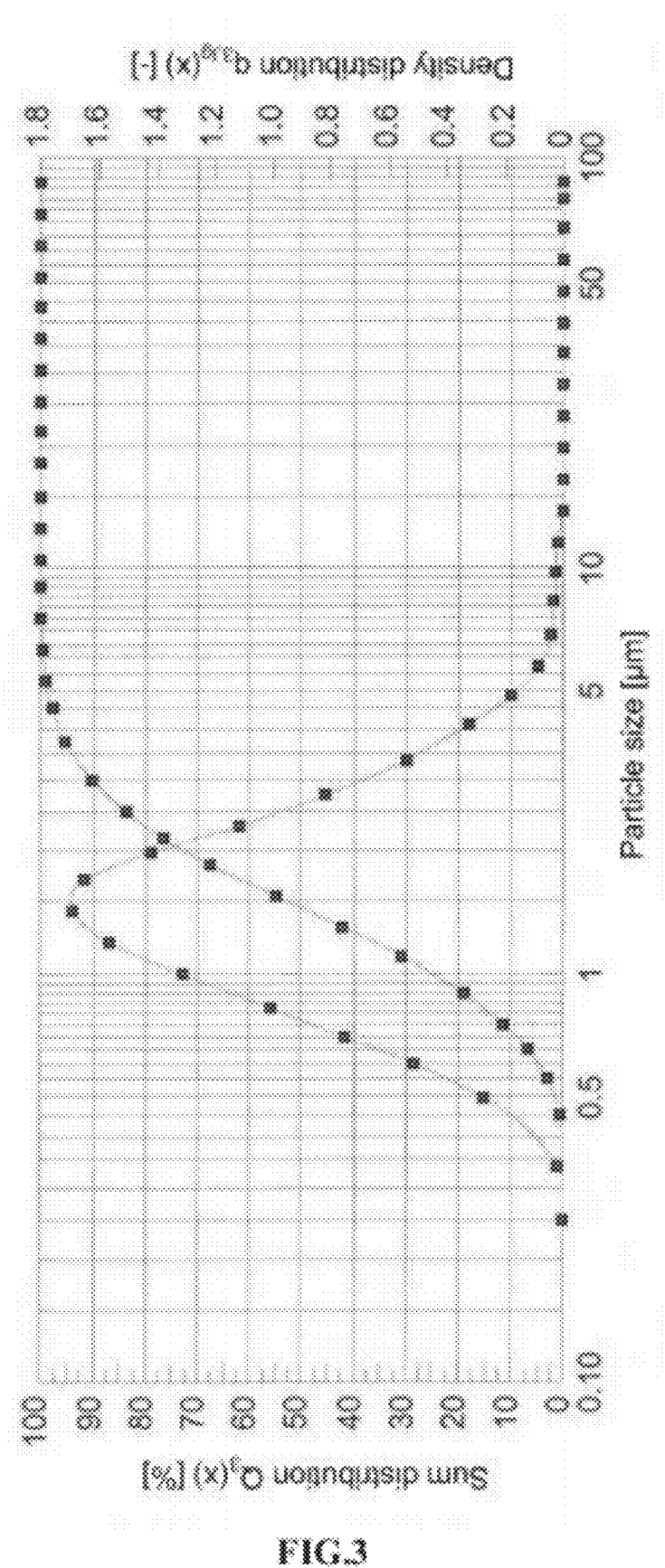
FIG. 3 is an example of phenytoin microparticles produced using a process of the invention. In example 5, the particle size distribution measured using a Sympatec Helos laser light diffraction particle sizer is as follows: $x_{10}$=0.73 micrometers, $x_{50}$=1.46 micrometers, and $x_{90}$=3.02 micrometers.

The invention claimed is:

1. A process for micronization of a pharmaceutically active agent comprising the steps of:
    (a) suspending the pharmaceutically active agent in a gaseous propellant or in a compressed gas,
    (b) processing this suspension by high pressure homogenization, and
    (c) obtaining dry powder upon depressurization;
    whereby the particle size of the pharmaceutically active agent is reduced by the micronization process.

2. A process for micronization of a pharmaceutically active agent comprising the steps of:
    (a) suspending the pharmaceutically active agent in a gaseous propellant,
    (b) processing this suspension by high pressure homogenization, and
    (c) obtaining a suspension of the micronized pharmaceutically active agent in the gaseous propellant;
    whereby the particle size of the pharmaceutically active agent is reduced by the micronization process.

3. The process according to claim 1 wherein the pharmaceutically active agent micronized by said process has an average particle size between about 0.1 and about 7.0 micrometers.

4. The process according to claim 1 wherein the pharmaceutically active agent micronized by said process has an average particle size of from about 0.5 to about 5.0 micrometers.

5. The process according to claim 1 wherein the suspension formed by the pharmaceutically active agent and the compressed gas or gaseous propellant comprises one or more pharmaceutically acceptable excipient.

6. The process according to claim 1 wherein the pharmaceutically active agent is poorly soluble in water and/or chemically or thermally unstable.

7. The process according to claim 1 wherein the pharmaceutically active agent comprises at least one of pimecrolimus (33-Epichloro-33-desoxy-ascomycin), 5-[(R)-2-(5,6-diethyl-indan-2-ylamino)-1-hydroxy-ethyl]-8-hydroxy-(1H)-quinolin-2-one, 3-methylthiophene-2-carboxylic acid (6S,9R,10S,11S,13S,16R,17R)-9-chloro-6-fluoro-11-hydroxy-17-methoxycarbonyl-10,13,16-trimethyl-3-oxo-6,7,8,9,10,11,12,13,14,15,16,17-dodecahydro-3H-cyclopenta-[α] phenanthren-17-yl ester, N-benzoylstaurosporine, oxcarbazepine, carbamazepine, 1-(2,6-Difluoro-benzyl)-1H-[1,2,3]triazole-4-carboxylic acid amide, cox-2 inhibitors, pyrimidylalaminobenzamides, camptothecin derivatives, proteins, peptides, vitamins, steroids, and bronchodilators.

8. The process according to claim 1 wherein the compressed gas comprises at least one of carbon dioxide, nitrogen, dimethyl ether, ethane, propane and butane.

9. The process according to claim 1 wherein the compressed gas is an HFA propellant qualified for human use.

10. The process according to claim 1 wherein the compressed gas is chosen from at least one of HFA134a and HFA227.

11. The process according to claim 5 wherein the pharmaceutically acceptable excipient comprises at least one of surfactant, carrier and lubricant.

12. The process according to claim 11 wherein the surfactant comprises at least one of acetylated monoglycerides, perfluorocarboxylic acid, polyethylene glycol (PEG) sterol esters, polyethylene oxide sorbitan fatty acid esters, sorbitan esters, sorbitan mono laureate, sorbitan mono oleate, sorbitan tri oleate, sorbitan mono palmitate, propylene glycol and oleic acid.

13. The process according to claim 1 wherein the suspension of the pharmaceutically active agent in a gaseous propellant or compressed gas is processed by homogenization using static geometries.

14. The process according to claim 1 wherein the suspension of the pharmaceutically active agent in a gaseous propellant or compressed gas is processed by homogenization using a dynamic valve.

15. The process according to claim 1 wherein the suspension of the pharmaceutically active agent and the compressed gas or gaseous propellant is formed in a first stirred vessel and stored in a second stirred vessel after the micronization process.

16. A process according to claim 1 wherein said micronized pharmaceutically active agent is filled directly to an inhalation device.

17. A process according to claim 2 wherein said micronized pharmaceutically active agent is filled directly to an inhalation device.

18. The process according to claim 1 wherein the particle size of the pharmaceutically active agent is reduced by the micronization process to an average particle size of about 7 micrometers or less than 7 micrometers.

19. The process according to claim 2 wherein the particle size of the pharmaceutically active agent is reduced by the micronization process to an average particle size of about 7 micrometers or less than 7 micrometers.

* * * * *